United States Patent [19]
Kaniss et al.

[11] 4,329,497
[45] May 11, 1982

[54] METHOD FOR THE PRODUCTION OF 4-HYDROXYPHENYLACETIC ACID

[75] Inventors: Normann Kaniss; Adolf Bauer, both of Raubling, Fed. Rep. of Germany

[73] Assignee: Diamalt Aktiengesellschaft, Munich, Fed. Rep. of Germany

[21] Appl. No.: 13,673

[22] Filed: Feb. 21, 1979

[30] Foreign Application Priority Data

Feb. 20, 1978 [DE] Fed. Rep. of Germany ....... 2807201

[51] Int. Cl.$^3$ ............................................. C07C 65/01
[52] U.S. Cl. ..................................... 562/478; 562/470
[58] Field of Search ................................ 562/478, 470

[56] References Cited
FOREIGN PATENT DOCUMENTS
1377243 12/1974 United Kingdom ................ 562/470

OTHER PUBLICATIONS
Fieser, L. F. et al., Reagents for Organic Synthesis, p. 863, 1967.

Primary Examiner—Paul J. Killos
Attorney, Agent, or Firm—Michael N. Meller; Anthony H. Handal

[57] ABSTRACT

Method for producing 4-hydroxyphenylacetic acid where
(a) o-chlorophenol is reacted with glyoxylic acid to form 3-chloro-4-hydroxymandelic acid,
(b) the 3-chloro-4-hydroxymandelic acid is reduced to 3-chloro-4-hydroxyphenylacetic acid, and
(c) the chloro group is cleaved from the 3-chloro-4-hydroxyphenylacetic acid.

3 Claims, No Drawings

METHOD FOR THE PRODUCTION OF 4-HYDROXYPHENYLACETIC ACID

4-Hydroxyphenylacetic acid is an important intermediate product in the synthesis of pharmaceutical preparations. There is, therefore, a general interest in achieving the most efficient synthesis possible.

Known methods are based, for example, on anisole which is converted into 4-methoxyphenylacetonitrile by chloromethylation and cyanidation (see Organikum, Berlin, 9th Edition, page 363). Saponification of the nitrile into acid, and subsequent cleavage of the ether with phosphorus/hydriodic acid (R. J. Meltzer et al., J. Org. Chem. 22 (1957) 1577) produces 4-hydroxyphenylacetic acid. The 4-stage synthesis however, has very unsatisfactory yields. The total yield, in relation to anisole, is generally below 21%.

Another known method, based upon phenol, through the Friedel-Crafts reaction leads to 4-hydroxyacetophenone which is converted into the desired compound by means of the Willgerodt-Kindler reaction (C. D. Joshi et al., J. Sci. Ind. Res. (New Delhi) Sect. B 21 (1962) 284). Here again, the total yield, in relation to phenol, of about 30% is extremely unsatisfactory. In addition, sulfides which are by-products of the reaction create a waste-water problem and the cost of overcoming it is disproportionately high.

The object was to find a method leading to 4-hydroxyphenylacetic acid without the disadvantages mentioned and with good yields. Surprisingly, it was found that an indirect approach which first appeared cumbersome solves this problem satisfactorily.

In the method according to the invention, (a) o-chlorophenol is reacted with glyoxylic acid to form 3-chloro-4-hydroxymandelic acid, (b) the 3-chloro-4-hydroxymandelic acid is reduced to 3-chloro-4-hydroxyphenylacetic acid, and (c) the chloro group is cleaved from the 3-chloro-4-hydroxyphenylacetic acid.

The reaction of phenol with glyoxylic acid is disclosed in Houben-Weyl, Methoden der organischen Chemie, Vol. VI/1c (1976) pages 1057–1058 and Canad. J. Chem. 44, 1966, pages 575–582. However, the resulting 4-hydroxymandelic acid cannot be reduced to 4-hydroxyphenylacetic acid in a simple manner.

The applicant has found that 3-chloro-4-hydroxymandelic acid can be produced by this method known for the production of 4-hydroxymandelic acid. However, in contrast to the unchlorinated compound, the 3-chloro-4-hydroxymandelic acid cannot be easily reduced to 3-chloro-4-hydroxyphenylacetic acid, from which the chloro group can be removed easily by reduction.

From Belgian Pat. No. 704,368 it is known to react mono- or disubstituted phenols either by means of Friedel-Crafts reaction to the corresponding acetophenone derivative and then, by the Willgerodt-Kindler reaction via the thiomorpholide derivative to the corresponding phenylacetic acid, or to convert them, after introducing suitable protective groups, into phenylacetic acids by chloromethylation and cyanidation followed by saponification. According to German Laid-Open Document No. 25 24 836, this method was improved by converting the o-chlorophenol for the protection of the hydroxyl group with a secondary alkyl halide into 2-chloralkoxy benzene which is then chloromethylated, cyanided and processed further. Although execution and yield of this method is superior to earlier methods, it was still not quite satisfactory. On the one hand, these known methods require at least four or five stages before reaching the 3-chloro-4-hydroxyphenylacetic acid stage, hence require a lot of labor, and result in only moderate yields of less than 50%. On the other hand, they involve process steps such as the production of thiomorpholide and the cyanidation of the chloromethyl stage which are hazardous to the environment and to health. The decomposition products of thiomorpholide derivatives contaminate the waste water completely and present a special problem in biological clarification. The mother liquors from the cyanidation process, which requires special safety measures in any case, also need a special treatment for the virtual quantitative removal of excess cyanide. If o-chlorophenol is reacted by the method of German Laid-Open Publication No. 25 24 836, to 3-chloro-4-hydroxyphenylacetic acid, the yield of 4-hydroxy-phenylacetic acid, obtained cleaving the choro group reductively, is only 40% in relation to the o-chlorophenol, and the obvious synthetic method which, as in the production of 3-chloro-4-hydroxyphenylacetic acid based on phenol passes through appropriate intermediate stages, also fails to produce satisfactory results.

The conversion of o-chlorophenol with glyoxylic acid in step (a) of the method according to the invention takes place in an alkaline solution. The selection of the mole ratios is not restricted, preferably an excess of glyoxylic acid is used. The reaction proceeds at temperatures between −5° and 100° C. After the reaction is completed, the free mandelic acid is released by acidification, the reaction product is extracted with an appropriate extracting agent, or is directly subjected to further reaction.

Since it was known that numerous other substituted phenols, for example, alkoxyphenols, produce, with glyoxylic acid and analogous compounds resin-like products, or result in totally unsatisfactory yields, it was surprising to find that glyoxylic acid attacks o-chlorophenol exclusively in the para position to the phenolic hydroxy group and ensures excellent yields. This is even more of a surprise since it is known that glyoxylic acid and similar compounds undergo disproportionation in alkaline solution, that unprotected phenols tend to autoxidation and resinification, especially in admixture with aldehydes, and that reacting chlorophenol with a compound such as glyoxylic acid may be expected to cause formation of isomers and difficult separation processes. Furthermore, the reluctance of phenolic mandelic acid to crystallize casts doubts upon the further processing of intermediate products.

For the reduction of 3-chloro-4-hydroxymandelic acid to 3-chloro-4-hydroxyphenylacetic acid in step (b) of the method according to the invention, various reducing agents known from the reduction of α-halogenphenylacetic acids and mandelic acids to the appropriate phenylacetic acids, such as the hydrogenation with a noble metal catalyst, reduction with sodium borohydride, reduction with nascent hydrogen, replacing the OH group by a halogen substituent which can be removed with tin/hydrochloric acid or zinc/glacial acetic acid or with hydrogen/catalyst or the reduction with hydriodic acid or iodine and phosphorus. The preferred reduction with hydriodic acid takes place in a suitable solvent such as glacial acetic acid; the hydriodic acid may be wholly or partly replaced by iodine+phosphorus. It is desirable to render the reaction medium containing the 3-chloro-4-hydroxyphenylacetic acid alkaline with soda lye, and to let the monosodium salt crystallize out. The salt is washed and redissolved in a small amount of water. After acidification and cooling, the 3-chloro-4-hydroxyphenylacetic acid is separated in crystal form.

Cleaving the chloro group in step (c) of the method according to the invention can be carried out in various ways, preferably by catalysis with hydrogen and a palladium catalyst.

From the literature a whole series of methods and examples is known for replacing halogen in organic compounds by hydrogen.

Besides dehalogenation by hydrogenation with a palladium catalyst, halogen can be split off by hydrogenation in alkaline solution on Raney nickel. Hydriodic acid and phosphorus or sodium in liquid ammonia may be used; reduction with nascent hydrogen is also known. Dehalogenation in an aromatic system generally requires drastic conditions and/or potent reducing agents; under certain circumstances, double bonds can be hydrogenated or other functional groups besides the halogen may be attacked and reductively eliminated.

For example, the dehalogenation of 3-chlorobenzoic acid to form benzoic acid with hydrogen/Raney nickel (Chem. Ber. 91 (1958) 1376) provides a yield of only 64%, compared to the reduction of chloroanilines and chloroanisoles which has a 90% yield.

By comparison, the reduction of the 3-chloro-4-hydroxyphenylacetic acid in step (c) of the method according to the invention by the preferred method produces a yield above 90% for the target product.

The process is carried out in an alkaline solution and at temperatures between room temperature and the boiling temperature of the reaction mixture. The hydrogen pressure may be equal to or in excess of the atmospheric pressure.

The total yield of the method according to the invention is about 65% of the o-chlorophenol used.

The method according to the invention is explained by the following reaction diagram:

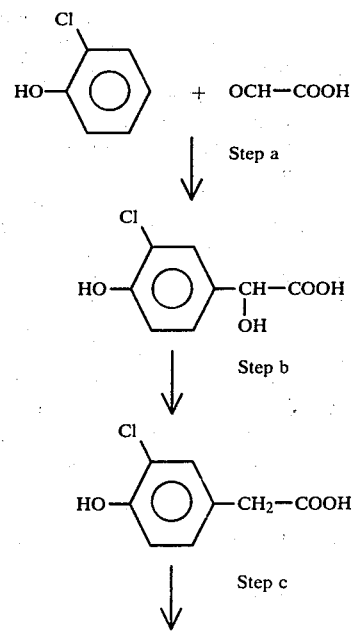

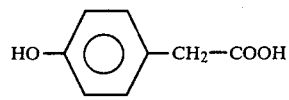

4-Hydroxyphenylacetic acid is used for the production of various pharmaceutical preparations.

According to U.S. Pat. No. 2,487,018 p-hydroxybenzylpenicillin sodium is obtained by adding 4-hydroxyphenylacetic acid to a penicillin culture. p-Hydroxybenzylpenicillin sodium is an antibiotic.

According to British Pat. No. 1,285,038 4-hydroxyphenylacetic acid is converted into 1-p-carbamoylmethylphenoxy-2,3-epoxypropane from which through reaction with isopropylamine the preparation of atenolol results, which is used as a beta-blocker.

According to German Laid-Open Document No. 26 21 090, starting with 4-hydroxyphenylacetic acid, 2-(p-hydroxyphenyl)-3-amino-1-propanol derivatives with broncholytic activity are obtained.

According to J. Med. Chem. 20, 1263 cont. (1977) one substitutes 4-hydroxyphenylacetic acid first in the 3-position, causes it to react, after protective group introduction, with tert.-butyl-benzylamine and reduces the reaction product to compounds with beta-adrenergic-like action.

EXAMPLE 7 liters of water are placed in a suitable reaction vessel. 1.75 kg of 50% glyoxylic acid solution are added and neutralized with 1.63 liters of 25% sodium hydroxide. At room temperature, a mixture of 0.39 kg of o-chlorophenol and 0.38 liter of 25% sodium hydroxide is added, heated to about 30° C. and allowed to react at this temperature while stirring for about 24 hours. The pH is adjusted to 1-2 with concentrated hydrochloric acid. The reaction mixture is evaporated in vacuo to about half of its volume, cooled and triple extracted with 1.5 liter of ethyl acetate each time. The combined ethyl acetate ester extracts are concentrated in vacuo to a considerable extent. The residue forms a light resin-like mass of 615 grams of 3-chloro-4-hydroxymandelic acid (corresponding to 98% of the theorectical value) which crystallizes in a few days when allowed to stand. A sample of the 3-chloro-4-hydroxymandelic acid recrystallized from a small amount of water has a melting point of 140°-141° C.

Analysis: Cl found: 17.7 and 17.3% Cl calculated: 17.53%.

In thin-layer chromatography the substance is homogeneous.

500 grams of crude 3-chloro-4-hydroxymandelic acid are dissolved in 2.5 liters of glacial acetic acid, mixed with 87 grams of red phosphorus, 31 grams of iodine, 30 ml of 57% hydriodic acid and 30 ml of water and are boiled under reflux for 2.5 hours. The product is drawn off from the unreacted phosphorus and concentrated to a considerable extent in vacuo. The residue is placed in 650 ml of water, is mixed with 1 liter of 25% sodium hydroxide and adjusted to a pH of 8-8.5. The sodium salt of the 3-chloro-4-hydroxyphenylacetic acid crystallizes out. This salt is processed into 3-chloro-4-hydroxyphenylacetic acid, obtaining 320 grams of this acid. The substance is very pure and has a melting point of 109°-110° C.

The yield of both stages amounts to 68.3% of the theoretical value, in relation to the o-chlorophenol used.

180 grams of 3-chloro-4-hydroxyphenylacetic acid are suspended in 350 ml of water and mixed with 240 ml of 25% sodium hydroxide. Heat is applied, 4 grams of palladium or charcoal added, the reaction vessel is closed, flushed repeatedly with nitrogen and hydrogen is introduced. At the same time, the reaction mixture is heated. At a pressure of about 5 atmospheres and a temperature of about 100° C., the reaction is completed within 7-8 hours. The mixture is filtered from the charcoal, the filtrate is adjusted to a pH of 1-2 with about 200 ml of concentrated hydrochloric acid. While cooling, stirring continues for some time and the crystallized substance is drawn off. After drying, 162 grams of crude product are obtained. After recrystallization 129 grams of pure 4-hydroxyphenylacetic acid (corresponding to 88% of the theoretical value) are obtained. By processing the mother liquors another 10 grams of pure acid are obtained, so that the total yield of this step is 96% of the theoretical value.

The 4-hydroxyphenylacetic acid has a melting range of 148°-152° C. and is identical with the authentic substance.

We claim:

1. A method for producing 4-hydroxyphenylacetic acid, which consists essentially of sequentially
   (a) reacting o-chlorophenol with glyoxylic acid in an alkaline solution at a temperature of from −5° to 100° C. to form 3-chloro-4-hydroxymandelic acid after acidification,
   (b) reducing the 3-chloro-4-hydroxymandelic acid by conventional means to 3-chloro-4-hydroxyphenylacetic acid, and
   (c) cleaving the chloro group from the 3-chloro-4-hydroxyphenylacetic acid in alkaline solution at between room temperature and the boiling point of the reaction mixture.

2. The method according to claim 1 wherein the reduction of step (b) is carried out with red phosphorus and iodine.

3. The method according to claim 2 or 1 wherein the chloro group cleavage in step (c) is carried out catalytically with hydrogen and a palladium catalyst.

* * * * *